United States Patent [19]
McEtchin et al.

[11] Patent Number: 5,439,391
[45] Date of Patent: Aug. 8, 1995

[54] LEAD ADAPTER

[75] Inventors: Stanley D. McEtchin, Pleasanton; D. Scott Romkee, San Jose; M. Elizabeth Bush, Fremont, all of Calif.

[73] Assignee: Ventritex, Inc., Sunnyvale, Calif.

[21] Appl. No.: 15,684

[22] Filed: Feb. 9, 1993

[51] Int. Cl.⁶ .......................................... H01R 29/00
[52] U.S. Cl. .................................. 439/518; 439/862; 439/863
[58] Field of Search .................. 439/169–175, 439/177, 295, 518, 839, 843, 891, 281, 836, 252, 863, 265, 346

[56] References Cited

U.S. PATENT DOCUMENTS

| | | | |
|---|---|---|---|
| 1,719,288 | 7/1929 | Danielson | 439/252 |
| 2,959,766 | 11/1960 | Jacobsen | 439/863 |
| 3,045,201 | 7/1962 | Hall | 439/172 |
| 3,210,720 | 10/1965 | Harris, Jr. | 439/518 |
| 3,924,922 | 12/1975 | Decenzo | 439/839 |
| 4,367,001 | 1/1983 | Munakata | 439/175 |
| 4,368,940 | 1/1983 | Sugiura | 439/170 |
| 4,583,543 | 4/1986 | Peers-Trevarton | 128/491 |
| 4,740,170 | 4/1988 | Lee et al. | 439/177 |
| 4,895,529 | 1/1990 | Thakrar et al. | 439/281 |
| 5,000,177 | 3/1991 | Hoffmann et al. | 128/419 |
| 5,007,864 | 4/1991 | Stutz, Jr. | 439/651 |
| 5,060,649 | 10/1994 | Höcherl et al. | 439/814 |
| 5,086,773 | 2/1992 | Ware | 128/419 |

FOREIGN PATENT DOCUMENTS

| | | | |
|---|---|---|---|
| 0400592 | 5/1990 | European Pat. Off. | |
| 0850326 | 9/1952 | Germany | 439/863 |
| 1206161 | 2/1984 | Italy | |

*Primary Examiner*—Gary F. Paumen
*Assistant Examiner*—Hien D. Vu
*Attorney, Agent, or Firm*—Steven M. Mitchell; Mark J. Meltzer; M. Elizabeth Bush

[57] ABSTRACT

An electronic connector pin adapter comprises a forward connector pin portion and a rear end portion. The rear end portion comprises a plurality of longitudinally extending retaining fingers carried in electrically connected relation with the connector pin portion and spaced about an open bore for connecting with and retaining an electronic connector pin, typically of different dimension from that of the forward connector pin portion.

25 Claims, 7 Drawing Sheets

LEAD ADAPTER

BACKGROUND OF THE INVENTION

This invention relates to adapters for electrical connectors, to permit an electrical connector to fit with a jack of a different size, with which it would not ordinarily fit. Thus, with such an adapter, electrical and electronic equipment is able to be connected to other electrical or electronic equipment with which it is not normally compatible because of differences in adapter and receptacle sizes.

More particularly, this invention relates to an adapter for electrically and mechanically coupling, in the field of cardiac pacemaking apparatus and the like, the terminal end of a sensing and/or pulse delivery lead of one size to a sensing and/or pulse delivery lead receptacle of another size.

Cardiac pacemaker and defibrillator systems are used to regulate the heartbeat. These devices may be surgically implanted in the body, and they may remain there for years. A typical implanted pulse generator, including the power supply and electronic circuits, operates by furnishing electrical pulses through a lead attached at the patient's heart, as required during disturbances in cardiac activity known as arrhythmia.

A pulse generator typically includes one or more receptacles, called connector cavities, into which the lead connectors may be inserted to form an electrical and mechanical connection. A lead connector typically comprises a pin for electrical contact, a sealing mechanism zone, and a hand grip zone. The lead connector pin is the electrically conductive element of the lead connector, and typically is mechanically and electrically connected to the connector contact of the connector cavity by a set screw. This retaining set screw may be loosened to permit withdrawal of the lead connector from the connector cavity, as for example when the pulse generator is to be replaced.

Conventional lead connectors and connector cavities customarily come in different sizes, which vary significantly among manufacturers. The current trend is to decrease the size of both lead connectors and connector cavities as materials and technologies allow, in order to reduce overall size of the implant. In view of the fact that the installed heart-stimulation lead generally lasts longer than the generator, it of course would be highly advantageous to reuse the implanted lead and thus avoid further surgery for explanation of the existing lead and implantation of a new lead, even when the lead connector is of a different size from the connector cavity of the replacement pulse generator.

This can be achieved by providing an adapter which is of the proper size to receive the implanted lead connector and plug into the replacement generator's connector cavity in a manner which establishes a reliable mechanical and electrical connection between the lead and the generator.

One such adapter is disclosed in U.S. Pat. No. 5,007,864 of Stutz. The device disclosed in this patent, however, accepts lead connectors of only a smaller size than the lead adapter, and is unable to be used with lead connectors which are larger than the connector cavity of the generator. Because the current trend is to reduce size as much as possible, it is likely that the replacement connector cavity will be smaller, not larger, so that in many commercial situations the Stutz invention will not be usable.

Another adapter is disclosed in U.S. Pat. No. 4,583,543 of Peers-Trevarton. The device of this patent also accepts lead connectors which are of only smaller size than the connector cavity of the generator. Thus it exhibits the same disadvantage as the previous design. Also, the device disclosed in this patent is relatively complex in design.

Other adapters are currently manufactured and function in part or primarily to extend a lead. This type of adapter comprises an adapter connector, similar to a lead connector, and a separate lead terminal receptacle similar to a connector cavity on a pulse generator, connected via a length of an insulated conductor. The resulting assembly is bulky in diameter and length. Such a receptacle typically uses a set screw mounted in a connector block which is covered by an elastomeric shell.

By this present invention, an adapter connector is capable of using standard lead design such as a pin having an elastomeric covering, so the difficulties of non-standard structure are avoided. Also in some embodiments a set screw connecting the adapter to the connector can be eliminated, for advantages of space saving and design simplification.

DESCRIPTION OF THE INVENTION

In accordance with this invention, an electronic connector pin adapter is provided, which comprises a forward connector pin portion and a rear end portion. The rear end portion comprises a plurality of longitudinally extending retaining fingers carried in electrically connected relation with the connector pin portion. The retaining fingers described above are spaced about an open bore for connecting with and retaining another electronic connector pin of different dimension from that of the forward connector pin portion. Thus, by this invention, the diameter of the forward connector pin portion may be substantially independent of the diameter of the electronic connector pin which is received in the open bore, so that the adapter of this invention provides great flexibility in facilitating the connection between electrical and electronic devices of virtually any type.

The connector pin adapter of this invention preferably comprises a solid rod of conductive metal, which is typically longitudinally spaced from the other electronic connector pin of different dimension that may be carried in the open bore of the connector pin adapter. Also, it is preferred in many embodiments for the fingers to be formed from the same piece of metal as the solid rod, for simplicity of construction and for optimal electrical connection.

In many embodiments, a compression collar surrounds the retaining fingers to urge the fingers inwardly in retentive relation with an electronic connector pin carried in the bore. The compression collar may define indentation means for receiving a pliers jaw or the like for sliding the compression collar over the fingers in tight, retentive manner.

Additionally, at least the rear end portion of the electronic connector pin and the compression collar are surrounded by a resilient, outer insulating covering. This outer insulating covering may define radially raised ring means for sealing while inserted in a connector cavity. Also, if desired the resilient outer covering may extend forwardly in sealing retention to a point which is intermediate the ends of the forward connector pin portion.

The fingers of the connector pin adapter may define first relatively thick portions adjacent their rear ends opposed to the forward connector pin portion. The compression collar, when present, may define a second, relatively thick portion which is positioned forwardly of the first relatively thick portion, to define an interference fit between the fingers and the compression collar. This contributes to good electrical and physical connection between the fingers and the electronic connector pin which is inserted into the open bore for connection with the adapter of this invention.

In another embodiment, the forward connector pin portion and the rear end portion may be separated by, and connected to, opposite ends of a flexible lead wire portion. Thus, the adapter of this invention may also function as a lead extension as well as a lead adapter.

In another embodiment, the connector pin adapter of this invention may have a forward connector pin portion which comprises a plurality of different, branching, electrically interconnected connector pins for making electrical connections to different electrical units. Typically, these connector pins may be carried for example in a branching Y connection or with a right angle connection relative to each other. Thus, simultaneous or sequential connections with different units may be provided, with the interconnected connector pins being of the same or differing sizes as may be desired.

In yet another embodiment, the rear end portion of the connector pin adapter may comprise an outer member defining a frustoconical bore facing away from the forward connector pin portion. An inner member is attached to the remainder of the connector pin adapter, being positioned within the frustoconical bore. The inner member defines the longitudinally extending retaining fingers about the open bore, so that as the other connector pin of different dimension from that of the forward connector pin portion is inserted, the retaining fingers are forced outwardly into frustoconical configuration for firm, gripping retention and electrical connection with the connector pin.

The inner member may be attached to the remainder of the connector pin in a variety of ways, for example by threaded engagement to the remainder of the connector pin adapter such as with a set screw, or with a threaded end as particularly shown in FIG. 4. Also, if desired, the inner member may be attached by a snap fit means.

It is also preferred in some circumstances for the fingers to have roughened inner faces for improved retention and connection with the other connector pin of different dimension which connects with the adapter.

Typically, the compression collar described above may be retained against longitudinal removal from the connector pin by flange means. This flange means may comprise the first and second relatively thick portions of the fingers and compression collar as described above, typically in conjunction with a flange disposed between the forward connector pin portion and the fingers of the rear end portion, so that the compression collar may be carried on the adapter without danger of it falling off, until it is placed into its compressing relation for use.

Thus, an electronic connector pin adapter is provided, having great versatility of use, coupled with simplicity of structure.

DESCRIPTION OF SPECIFIC EMBODIMENTS

Figure 1:
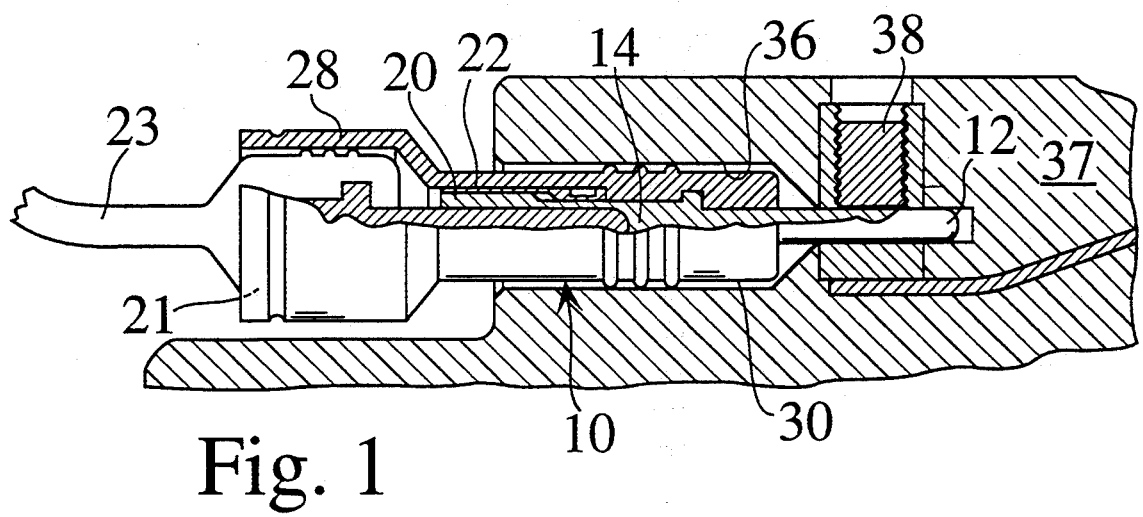
FIG. 1 is an elevational view, taken partially in section, of an electronic connector attached to the adapter of this invention, mounted in the connector cavity of a pulse generator.
Figure 2:
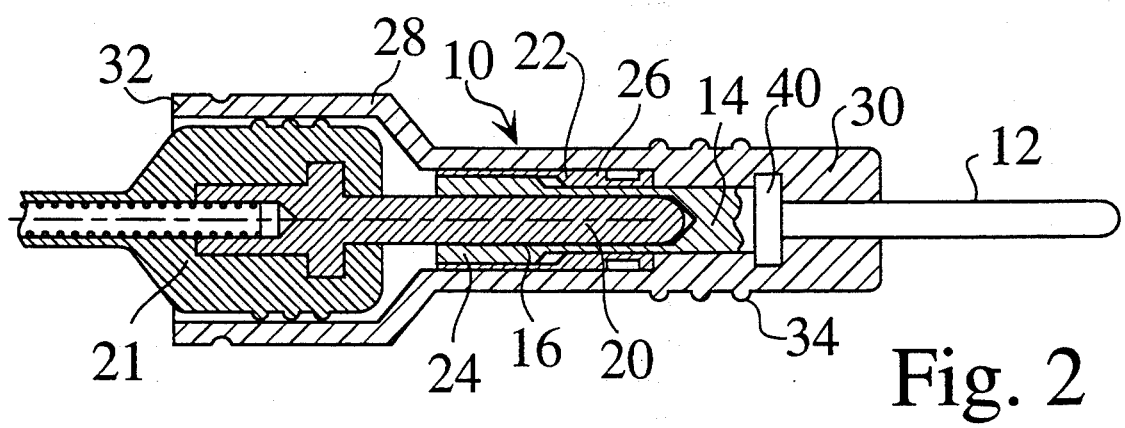
FIG. 2 is a longitudinal sectional view of the adapter of this invention, showing its connection with another electronic connector pin of different dimension from that of the forward connector pin portion of the adapter.
Figure 3:
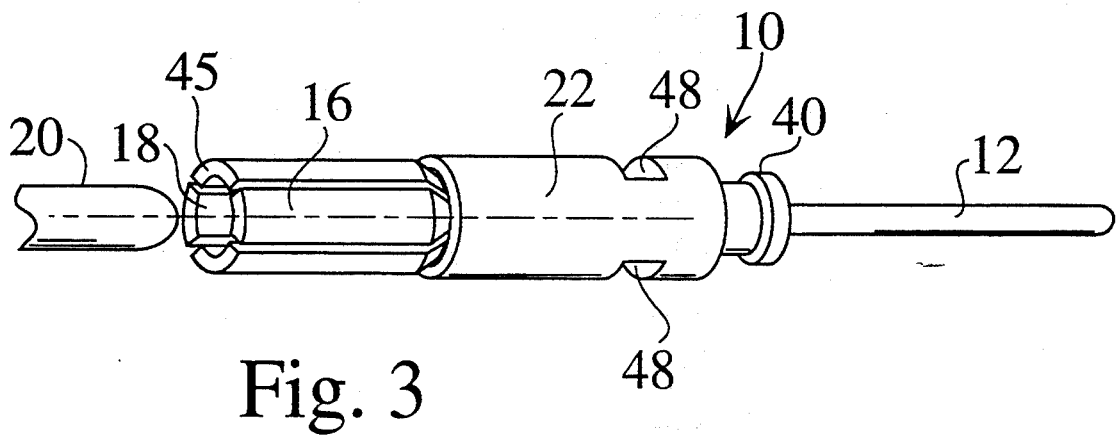
FIG. 3 is a perspective view of the connector pin adapter of FIGS. 1 and 2, showing the compression collar prior to its application over the fingers, and also showing a connector pin about to enter into the bore defined between the fingers.
Figure 4:
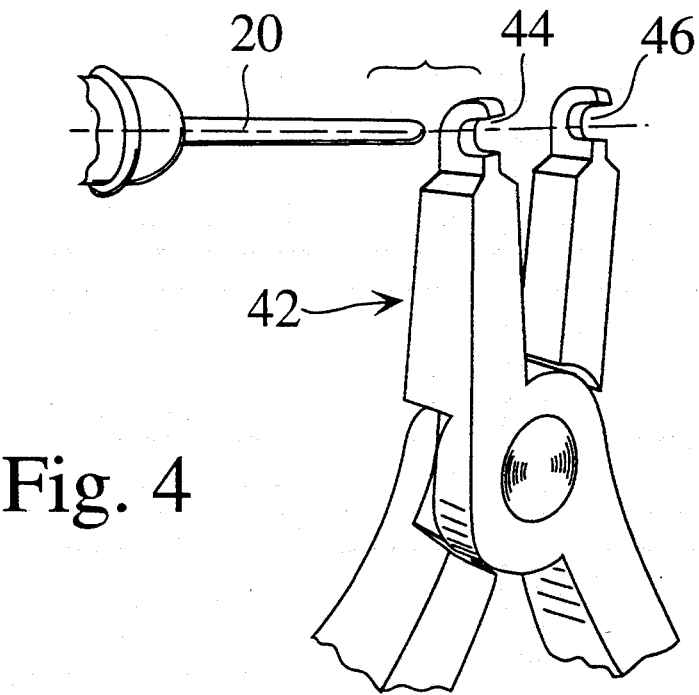
FIG. 4 is a perspective view of the pliers used herein, and the connector pin.
Figure 5:
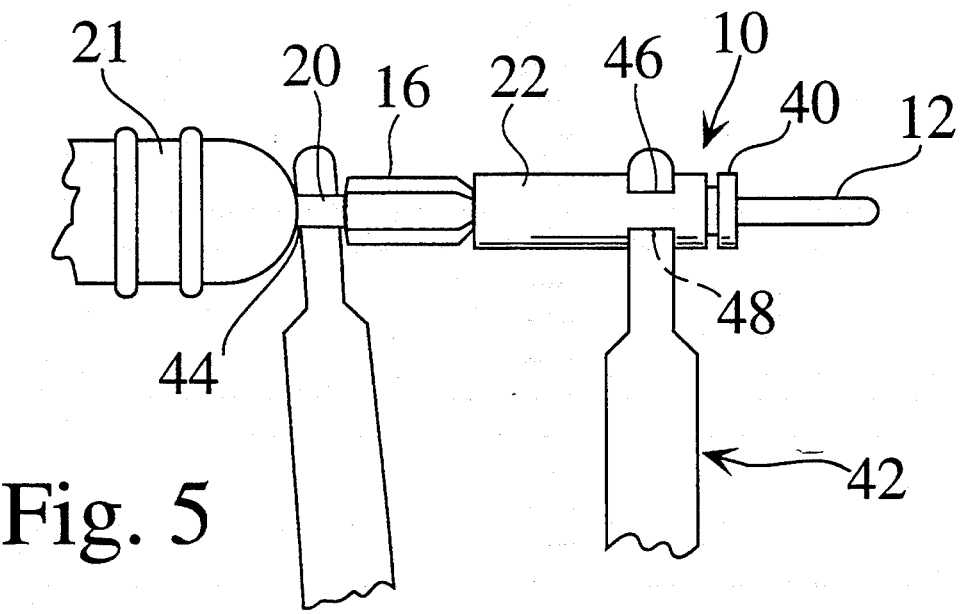
FIGS. 5 and 6 are elevational views respectively showing steps of the process with the device of FIG. 3.

Referring to FIGS. 1-3, electronic connector pin adapter 10 comprises a forward connector pin portion 12 and a rear end portion 14. Rear end portion 14 comprises a plurality of longitudinally extending retaining fingers 16 (FIG. 3). Fingers 16 are each formed from the same piece of metal as the solid rod that comprises forward connector pin portion 12, for the best possible electrical connection between fingers 16 and connector pin 12.

Fingers 16 are shown to be spaced about an open bore 18, which is shown to be in FIGS. 1 and 2 to be occupied by an electronic connector pin 20 which is of larger dimension than the forward connector pin portion 12. Alternatively, connector pin 20 may be of smaller dimension than connector pin 12, this being easily accomplished by proper adjustment of the diameter of rear end portion 14 and especially the diameter of bore 18 of fingers 16. Alternatively, fingers 16 may be pressed inwardly to varying degrees by compression collar 22 to accommodate for varying sizes of connector pins 20.

Compression collar 22 surrounds the retaining fingers 16 to urge fingers 16 inwardly into retentive relation with connector pin 20 as it is carried in bore 18. If desired, the inner surfaces of retaining fingers 16 may be roughened to improve the frictional retention of connector pin 20, as well as the electrical connection between fingers 16 and connector pin 20.

In this embodiment, fingers 16 define first relatively thick portions 24 adjacent their rear ends which are opposed to the forward connector pin portion 12. Compression collar 22, on the other hand, defines a second, annular, relatively thick portion 26 positioned forwardly of first relatively thick portion 24, to define an interference fit between fingers 16 and compression collar 22.

The rear end portion 14 and compression collar 22 are surrounded by a resilient, outer insulating covering 28, which may be made of a conventional elastomeric material. Outer insulating covering 28 may have a forward portion 30 that extends forwardly in sealing relation to a point intermediate the ends of forward connector pin portion 12. Rearward portion 32 of outer covering 28 may comprise an enlarged receptacle member to receive the handle 21 of connector pin 20 in sealing relation. Outer covering 28 may define raised rings 34 for sealing, for insertion into connector cavity 36, as shown particularly in FIG. 1. Connector pin portion 12 may be conventionally retained in the connector cavity 36 of a pulse generator 37 by a set screw 38.

Accordingly, essentially any electronic connector pin 20, of essentially any size, may be connected to a connector pin adapter of this invention, to facilitate the connection of a pin 20 of essentially any size to a connector cavity 36 of any size, with the actual connection in the receptacle being provided by connector pin portion 12. This is accomplished with simple and inexpensive structure, being readily attachable and removable from connector pin 20 as may be desired.

Referring to FIGS. 3 to 6, one embodiment of the connection process is disclosed.

FIG. 3 shows the connector pin adapter of this invention with compression collar 22 carried on the adapter 10, being retained against removal from the end of connector pin 12 by the presence of flange 40, which may be welded or otherwise attached onto connector pin adapter 10. Compression collar 22 may be retained from falling off of its other end by the diameter of fingers 16 in their natural, uncompressed configuration. Resilient outer covering 28 is not yet applied in the configuration of FIG. 3.

As a first step, a pin 20 may be manually inserted into bore 18 of adapter 10. Then, as in FIG. 5, connector pin adapter 10 and connector pin 20 are brought together by pliers 42, having jaws which each carry a recess 46, 44 for respectively receiving adapter 10 and connector pin 20, with connector pin 20 occupying bore 18 within fingers 16. Recess 46 of the pliers jaws fits around indentations 48 of compression collar 22 for gripping of the same, while the other indentation 44 of the pliers jaws surrounds a portion of connector pin 20, with that jaw abutting the outer ends 45 of fingers 16.

Figure 6:
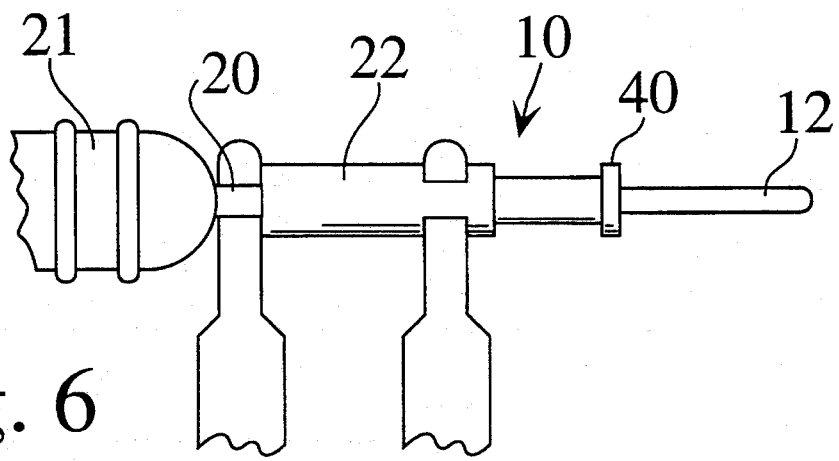

Then, upon compression of the pliers, the configuration of FIG. 6 is formed, in which compression collar 22 slides over fingers 16 to compress them inwardly, firmly and tightly against connector pin 20, for firm retention thereof in an electrically connecting mode. The outer insulating covering 28 is then slid over the end of this assembly. Thus, thereafter the user may grasp handle 21 to insert connector pin portion 12 into the desired receptacle, for electronic connection of a circuit which includes connector pin 20 and the electronics to which it is connected.

Figure 7:
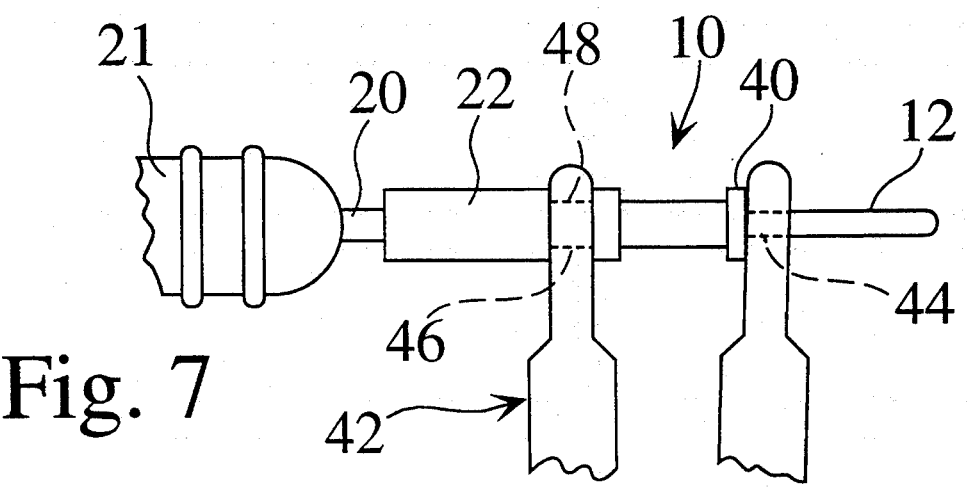
FIG. 7 is another elevational view showing how the device of FIG. 6 may then be disconnected.

To disconnect the same structure, the outer covering 28 is removed, and, as in FIG. 7, the pliers jaws can be fitted so that recess 44 and its jaw fits connector pin portion 12 and abuts against flange 40, while the pliers jaw with recess 46 enters into engagement with indentations 48. Then, compression of the pliers again causes the connector pin adapter 10 to resume the configuration shown in FIG. 5.

Figure 8:
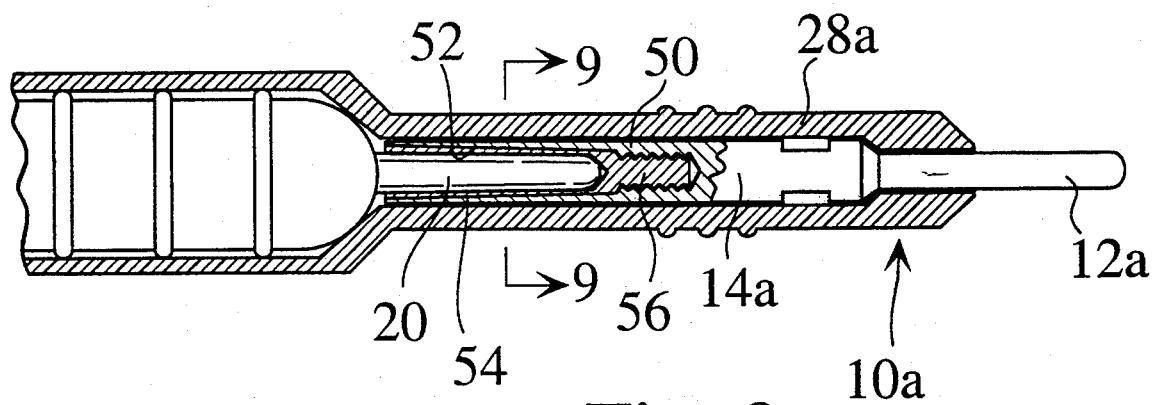
FIG. 8 is an elevational view, taken partly in longitudinal section, of another embodiment of the electronic connector pin adapter of this invention, shown in connected relation with another electronic connector pin of different dimension.
Figure 9:
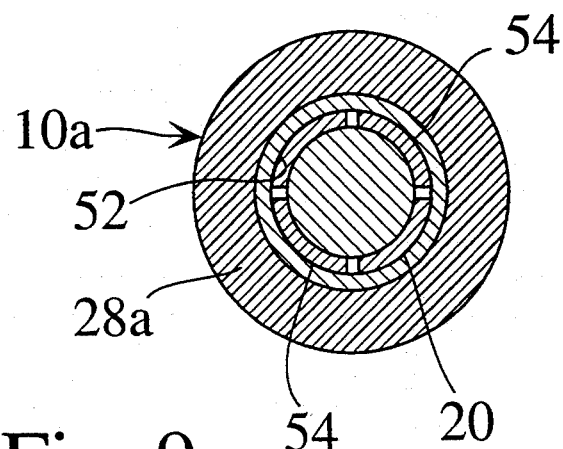
FIG. 9 is a sectional view, taken along line 9—9 of FIG. 8.

Referring to FIGS. 8 and 9, another embodiment of the connector adapter system of this invention is shown, with connector pin adapter 10a being shown to be in connection with electronic connector pin 20 as in the previous embodiment.

In this embodiment, forward connector pin portion 12a is connected to a rear end portion 14a in a manner generally similar to the previous embodiment, except in this circumstance rear end portion 14a defines an integral metal outer sleeve 50 without finger-defining slots. Sleeve 50 of the rear end portion comprises an outer member, which defines a frustoconical bore 52 which faces away from forward connector portion 12a. An inner member 54 is attached to outer member 50 by a screw thread projection 56, engaged in a socket defined by outer member 50. Inner member 54 comprises longitudinally extending retaining fingers within the bore 52 defined by outer member 50, which defines an open bore which is occupied by connector pin 20.

Thus, because of the frustoconical tapering of bore 52, typically about two to four degrees, as connector pin 20 enters the open bore defined by fingers 54, the fingers 54 are forced outwardly in a similar frustoconical configuration to provide a strong, mating, conical connection which firmly holds connector pin 20 in place.

The system may be adjusted by the amount of advancement of screw end 56 into its socket, to accommodate for size variations of connector pin 20.

As before, resilient outer covering 28a is provided.

Figure 10:
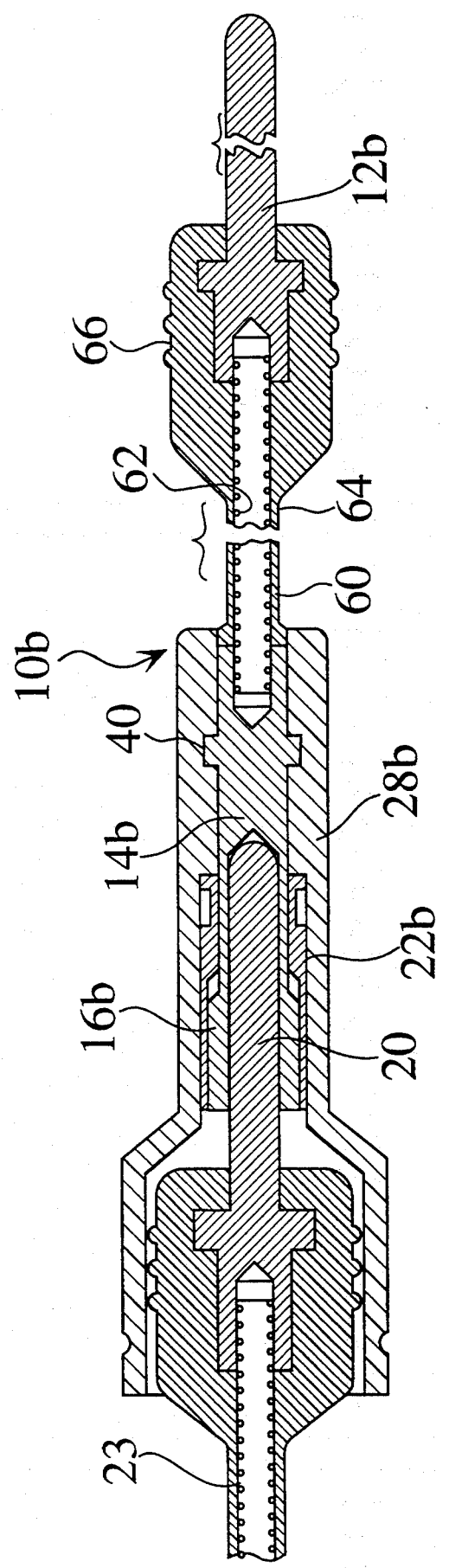
FIG. 10 is a longitudinal section of a third embodiment of the electronic connector pin adapter of this invention, connected with another electronic connector pin of different dimension.

Referring to FIG. 10, another modification of the connector pin adapter of this invention is shown. As before, electronic connector pin 20, which is of the wrong size for connection to a receptacle, may be received by the rear end portion 14b of connector pin adapter 10b of this invention. Rear end portion 14b can be seen to be of substantially similar design to rear end portion 14 shown particularly in FIG. 2, having longitudinal fingers 16b which are forced inwardly by compression collar 22b, and surrounded by insulative, resilient, outer covering 28b as in the previous embodiment.

However, in accordance with this embodiment, rear end portion 14b is electrically connected at its forward end with a length of lead cable 60, which conventionally comprises a coiled conductor 62 or a plurality of multifilar, coiled conductors, enclosed with insulation 64. This cable is typically flexible, and connects with a plastic housing or handle 66 which is emplaced about the rear end of forward connector pin portion 12b, which typically defines a connector pin of different diameter from connector pin 20. Thus, connector pin portion 12b can be seen to be in electrical connection through cable 60 with rear end portion 14b, which, in turn, is in electrical connection with connector pin 20 through the connection of fingers 16b, which are compressed into good, electrical connection by the action of compression collar 22b.

Accordingly, this embodiment serves both as a connector and a connector extension, since cable 60 can of course be of any desired length. If the cable 23 of connector pin 20 is too short for a desired purpose, the embodiment of FIG. 10 may be used to extend the connector. In this case the connector pin portion 12b may be of the same diameter as connector pin 20 if desired, or, it may be of a different diameter, either larger or smaller, as is needed to make the desired connection with a receptacle.

Figure 11:
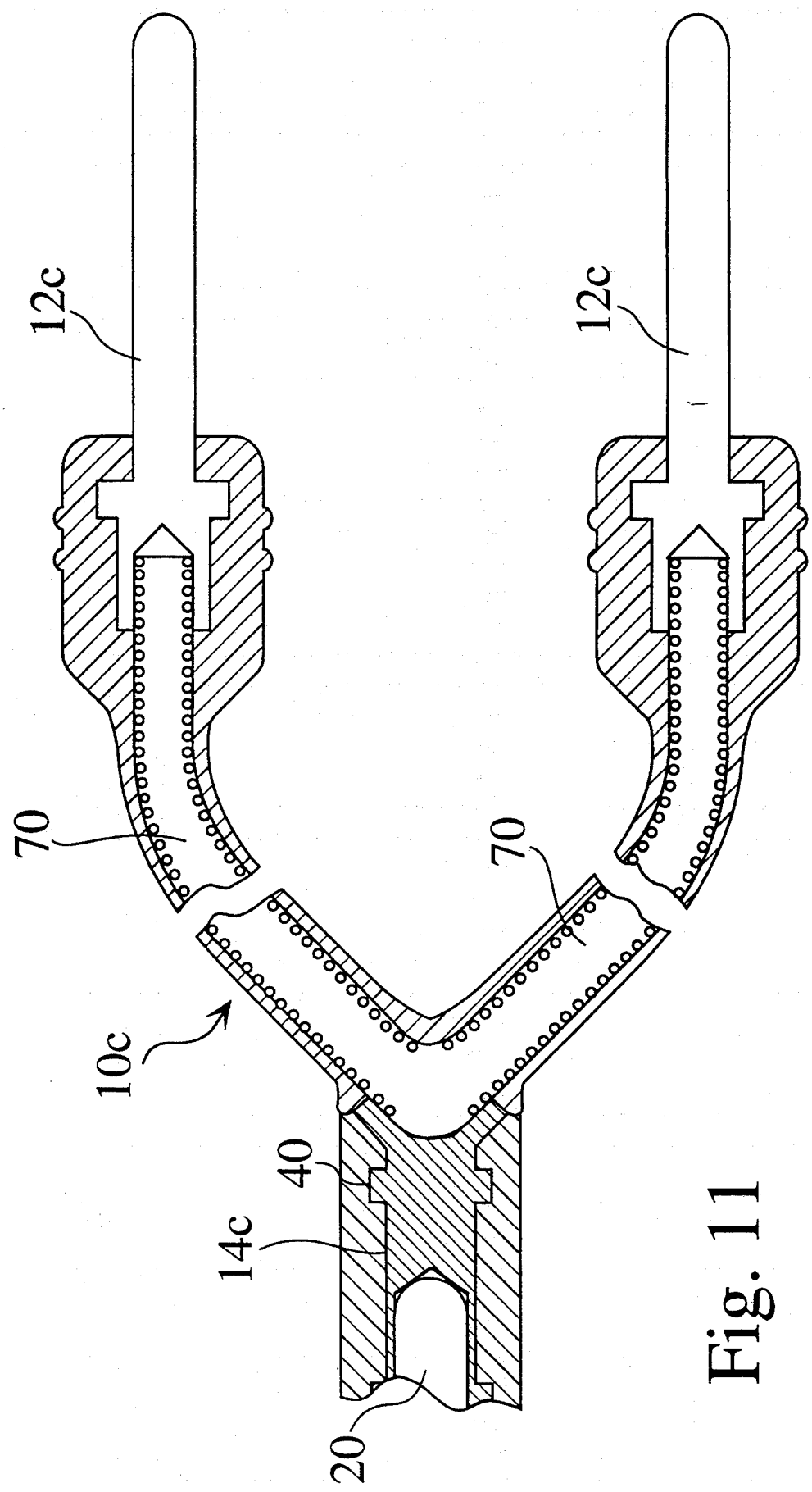
FIG. 11 is a longitudinal sectional view of a fourth embodiment of the electronic connector adapter of this invention, connected with another electronic connector pin of different dimension.

Referring to FIG. 11, another embodiment 10c of the connector pin adapter of this invention is shown. As before, the same electronic connector pin 20 may be positioned in the rear end portion 14c of the connector pin adapter of this embodiment. Rear end portion 14c may be similar in design to rear end portion 14 as shown in FIG. 2.

However, in this embodiment, rear end portion 14c connects with branched connector cable portions 70, which, in turn, each connect with a pair of forward connector pin portions 12c. Portions 12c are generally similar in construction to the forward connector pin portion 12 of FIG. 2. Thus, by this embodiment, the single connector pin 20 may be multiplied into two or more connector pins 12c which are each in electrical connection with connector pin 20, for connection to multiple receptacles. The respective connector pins 12c may be of the same or different dimensions from pin 20 as is desired, for simultaneous connection with a pair of receptacles if desired, or alternate connection with receptacles of differing sizes, if that is desired. Thus, a great improvement in the versatility of electronic connection systems is provided by this embodiment.

Figure 12:
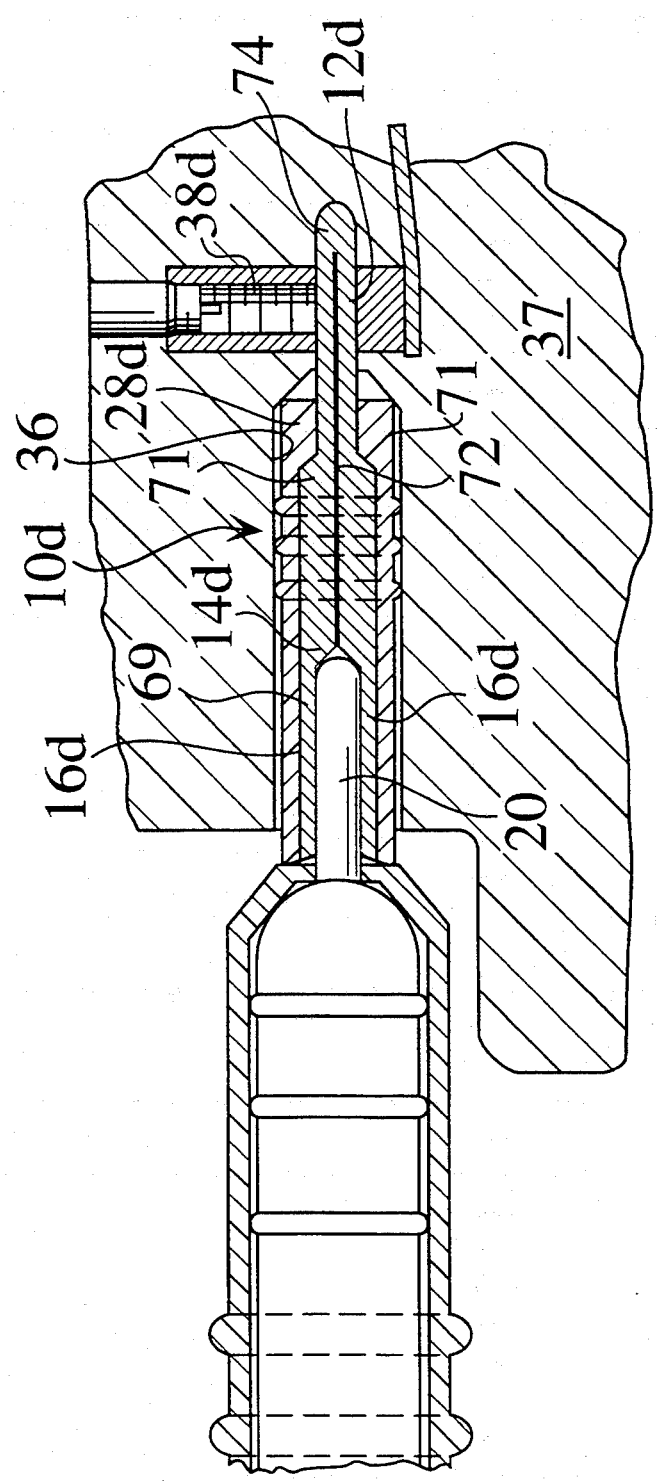
FIG. 12 is a longitudinal sectional view of yet another embodiment of this invention.

FIG. 12 shows another embodiment of the connector pin adapter of this invention. As before, electronic connector pin 20, of the wrong size for connection to a receptacle, may be received by the rear end portion 14d of connector pin adapter 10d. Rear end portion 14d comprises a longitudinally bifurcated member to thus define a pair of longitudinal fingers 16d which are spaced to form an aperture to receive connector pin 20 along some of their length 69, and which are closely spaced to each other along another portion of their length 71, being separated there only by narrow slot 72. In this embodiment, fingers 16d are integrally joined together at common junction area 74 in forward connector portion 12d, which may otherwise be basically similar in structure and function to the forward connector portions 12 of previous embodiments.

Set screw 38d retains connector pin portion 12d in the connector cavity 36 of pulse generator 37, and also clamps down on connector pin portion 12d to transmit compressive force onto fingers 16d, to electrically and mechanically join them to connector pin 20.

Thus, by control of set screw 38d, fingers 16d can be brought into gripping relation with connector pin 20 for firm gripping thereof and electrical connection therewith.

Resilient outer covering 28d may then be provided in a manner similar to that of previous embodiments. Alternatively, resilient outer covering 28d may already be in place prior to assembly of the adaptor 10 onto the connector pin 20.

An advantage of this embodiment is that the set screw which is already present, as shown for example in the other embodiment of FIG. 1 as set screw 38, is given an added function. As set screw 38d presses down on the two portions of connector pin portion 12d, separated by slot 72, set screw 38d also facilitates the electrical/mechanical contact between connector pin 20 and pin portion 12d, while also providing electrical contact between pin portion 12d and circuitry which is connected to set screw 38. Thus, a simplified electrical connection is provided between connector pin 20 and such circuitry, even though connector pin 20 is of the wrong size for such connection. The system of this embodiment eliminates the use of pliers and provides simplification of the system.

Also, resilient outer covering 28d can be in place as provided by the manufacture or otherwise prior to use, since set screw 38d can be engaged and tightened even with the presence of covering 28d. Thus, the doctor in the operating room has one less assembly step with this embodiment.

The above has been offered for illustrative purposes only, and is not intended to limit the scope of the invention of this application, which is as defined in the claims below.

That which is claimed is:

1. An electronic connector pin adapter, which comprises:
   a forward connector pin portion;
   a rear end portion comprising a plurality of longitudinally extending retaining fingers in electrically connected relation with said forward connector pin portion and spaced about an open bore for connecting with and retaining an electronic connector pin different from that of the forward connector pin portion;
   a flange integral with and disposed between said forward connector pin portion and the fingers of said rear end portion; and
   a compression collar surrounding said retaining fingers, longitudinally movable with respect to said fingers, to urge said fingers inwardly in retentive relation with said electronic connector pin in said bore.

2. The connector pin adapter of claim 1 in which said forward connector pin portion comprises a solid rod of conductive metal, said fingers being formed from the same piece of metal as said solid rod.

3. The connector pin adapter of claim 1 in which said compression collar defines indentation means for receiving a pliers jaw for sliding said compression collar over said fingers.

4. The connector pin adapter of claim 1 in which at least said rear end portion and compression collar are surrounded by a resilient, outer insulating covering.

5. The connector pin adapter of claim 4 in which said outer covering defines radially raised ring means for making sealing contact with periphery of a connector cavity.

6. The connector pin adapter of claim 4 in which said forward connector pin portion has two ends and said resilient outer covering extends forwardly in sealing retention of a point intermediate said ends of said forward connector pin portion.

7. The connector pin adapter of claim 1 in which said fingers define first relatively thick portions adjacent their rear ends opposed to the forward connector pin portion, while said compression collar defines a second, relatively thick portion positioned forwardly of said first relatively thick portions, to define an interference fit between said fingers and compression collar.

8. The connector pin adapter of claim 1 in which said forward connector pin portion and said rear end portion are separated by and connected to opposite ends of a flexible lead wire portion.

9. The connector pin adapter of claim 1 in which said forward connector pin portion comprises a plurality of different, electrically interconnected connector pins for making electrical connections with different connector cavities.

10. The connector pin adapter of claim 1 in which said fingers have roughened inner faces for improved retention and connection with said different connector pin.

11. The connector pin adapter of claim 1 in which said compression collar is retained against longitudinal removal from said connector pin adapter by said flange.

12. The connector pin adapter of claim 1 in which said forward connector pin portion is longitudinally spaced from said different connector pin as carried in said connector pin adapter.

13. An electronic connector pin adapter, which comprises;
   a forward connector pin portion;
   a rear end portion comprising a plurality of longitudinally extending fingers in electrically connected relation with said forward connector pin portion and spaced about an open bore, for connecting with and retaining another electronic connector pin in a portion longitudinally spaced from said forward connector pin portion;
   a flange integral with and disposed between said forward connector pin portion and the fingers of said rear end portion; and
   a compression collar surrounding said retaining fingers, longitudinally movable with respect to said fingers, to urge said fingers inwardly in retentive relation with said other electronic connector pin in said bore, wherein said compression collar is retained against longitudinal removal from said forward connector pin portion by said flange.

14. The connector pin adapter of claim 13 in which at least said rear end portion and compression collar are surrounded by a resilient, outer insulating covering.

15. The connector pin adapter of claim 14 in which said fingers define relatively thick portions adjacent their rear ends opposed to the forward connector pin portion, while said compression collar defines a second, relatively thick portion positioned forwardly of said first relatively thick portions, to define an interference fit between said fingers and compression collar.

16. The connector pin adapter of claim 15 in which said fingers have roughened inner faces for improved retention and connection with said other electronic connector pin.

17. The connector pin adapter of claim 15 in which said compression collar defines indentation means for receiving a pliers jaw for sliding said compression collar over said fingers.

18. The connector pin adapter of claim 15 in which said forward connector pin portion comprises a solid rod of conductive metal, said fingers being formed from the same piece of metal as said solid rod.

19. An electronic connector pin adapter, comprising:
   a forward connector pin portion having two ends;
   a rear end portion comprising a plurality of longitudinally extending retaining fingers in electrically connected relation with one of said two ends of said forward connector pin portion and spaced about an open bore for connecting with and retaining an electronic connector pin different from that of the forward connector pin portion;
   a flange integral with and disposed between said forward connector pin portion and the fingers of said rear end portion, wherein said flange provides a surface for abutment of a pliers jaw for disconnection of said electronic connector pin adapter from the electronic connector pin;
   a compression collar surrounding said retaining fingers to urge said fingers inwardly in retentive relation with said electronic connector pin in said bore; and
   a resilient, outer insulating covering surrounding at least said rear end portion and compression collar, and extending forwardly in sealing retention of a point intermediate said ends of said forward connector pin portion.

20. The electronic connector pin adapter of claim 19, wherein said compression collar defines indentation means for receiving a pliers jaw for sliding said compression collar over said fingers.

21. The electronic connector pin adapter of claim 19, wherein said forward connector pin portion is longitudinally spaced from said connector pin as carried in said connector pin adapter.

22. The electronic connector pin adapter of claim 19, wherein said forward connector pin portion and said rear end portion are separated by and connected to opposite ends of a flexible lead wire portion.

23. The electronic connector pin adapter of claim 19, wherein said forward connector pin portion comprises a plurality of electrically interconnected connector pins for making electrical connection with different connector cavities.

24. The electronic connector pin adapter of claim 19, wherein said compression collar is retained against longitudinal removal from said forward connector pin portion by said flange.

25. The electronic connector pin adapter of claim 19, wherein said fingers define first relatively thick portions adjacent their rear ends opposed to the forward connector pin portion, while said compression collar defines a second, relatively thick portion positioned forwardly of said first relatively thick portions, to define an interference fit between said fingers and compression collar, and wherein said compression collar is retained against accidental longitudinal removal from said rear end portion by said interference fit.

* * * * *